(12) United States Patent
Schlienger et al.

(10) Patent No.: US 9,011,440 B2
(45) Date of Patent: Apr. 21, 2015

(54) BONE SCREW

(75) Inventors: André Schlienger, Arlesheim (CH); Peter Senn, Waldenburg (CH)

(73) Assignee: DePuy Synthes Products, Inc., Raynham, MA (US)

( * ) Notice: Subject to any disclaimer, the term of this patent is extended or adjusted under 35 U.S.C. 154(b) by 175 days.

(21) Appl. No.: 13/424,918

(22) Filed: Mar. 20, 2012

(65) Prior Publication Data

US 2012/0203226 A1 Aug. 9, 2012

Related U.S. Application Data

(63) Continuation of application No. 11/259,537, filed on Oct. 25, 2005, now Pat. No. 8,162,998, which is a continuation of application No. PCT/CH2004/000095, filed on Feb. 23, 2004.

(51) Int. Cl.
```
A61B 17/72      (2006.01)
A61B 17/68      (2006.01)
A61B 17/86      (2006.01)
```

(52) U.S. Cl.
CPC .............. *A61B 17/686* (2013.01); *A61B 17/72* (2013.01); *A61B 17/7241* (2013.01); *A61B 17/725* (2013.01); *A61B 17/863* (2013.01)

(58) Field of Classification Search
USPC ............ 606/62–68, 301–321, 286–296
See application file for complete search history.

(56) References Cited

U.S. PATENT DOCUMENTS

| | | | | |
|---|---|---|---|---|
| 2,382,019 A * | 8/1945 | Miller | | 411/378 |
| 4,711,232 A * | 12/1987 | Fischer et al. | | 606/67 |
| 4,760,843 A * | 8/1988 | Fischer et al. | | 606/304 |
| 5,931,838 A * | 8/1999 | Vito | | 606/281 |
| 5,954,722 A * | 9/1999 | Bono | | 606/281 |
| 6,162,234 A * | 12/2000 | Freedland et al. | | 606/151 |
| 6,227,430 B1 * | 5/2001 | Rosen et al. | | 228/2.1 |
| 6,355,043 B1 * | 3/2002 | Adam | | 606/62 |
| 6,575,975 B2 * | 6/2003 | Brace et al. | | 606/86 B |
| 7,195,633 B2 * | 3/2007 | Medoff et al. | | 606/309 |
| 7,655,009 B2 * | 2/2010 | Grusin | | 606/64 |
| 7,662,379 B2 * | 2/2010 | Presta | | 424/133.1 |
| 7,682,379 B2 * | 3/2010 | Mathieu et al. | | 606/289 |
| 7,850,690 B2 * | 12/2010 | Frigg et al. | | 606/67 |
| 8,388,665 B2 * | 3/2013 | Eberlein et al. | | 606/290 |
| 2003/0028193 A1 * | 2/2003 | Weil et al. | | 606/73 |
| 2003/0187447 A1 * | 10/2003 | Ferrante et al. | | 606/73 |
| 2003/0199876 A1 * | 10/2003 | Brace et al. | | 606/69 |
| 2004/0158252 A1 * | 8/2004 | Prager et al. | | 606/72 |
| 2005/0065526 A1 * | 3/2005 | Drew et al. | | 606/72 |
| 2005/0075635 A1 * | 4/2005 | Semet | | 606/64 |

FOREIGN PATENT DOCUMENTS

WO 2004/089230 10/2004

* cited by examiner

*Primary Examiner* — Jerry Cumberledge

(74) *Attorney, Agent, or Firm* — Fay Kaplun & Marcin, LLP

(57) ABSTRACT

A system and method are for bone fixation. A radially expandable sleeve is inserted over an elongated shaft of a bone screw. The bone screw and radially expandable sleeve are inserted into a transverse opening extending through a bone fixation device positioned in a bone until the radially expandable sleeve is fully housed within the transverse opening. The bone screw is further screwed into the bone relative to the radially expandable sleeve to cause expansion of the radially expandable sleeve within the bone fixation device, thereby locking the sleeve to the bone fixation device.

13 Claims, 3 Drawing Sheets

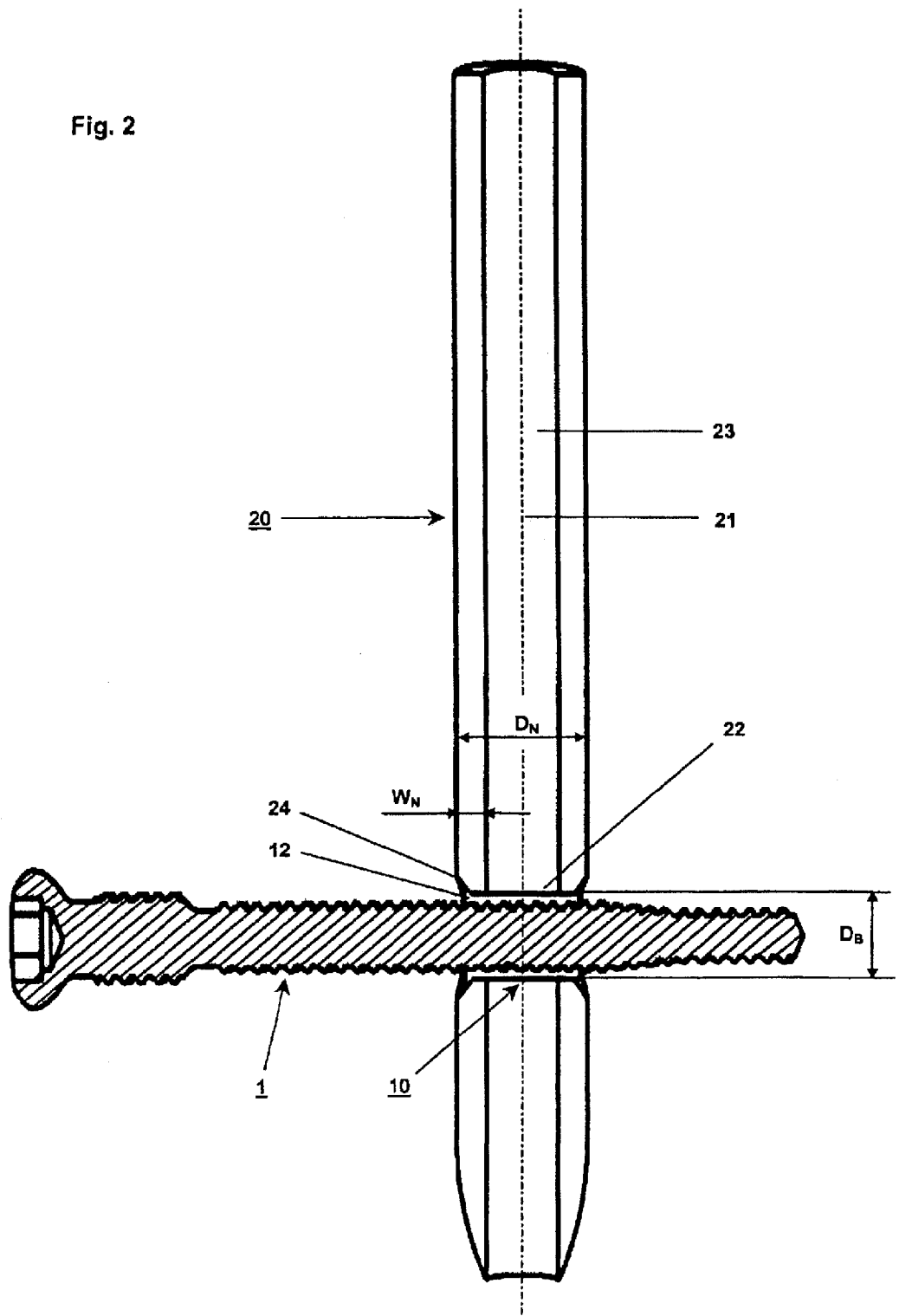

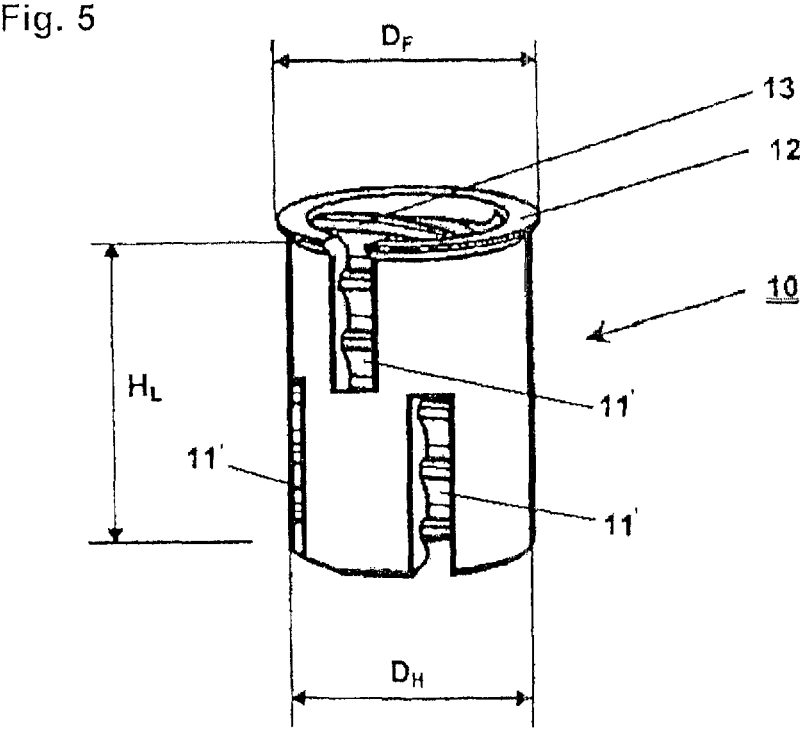

BONE SCREW

CROSS REFERENCE TO RELATED APPLICATION

The present application is a continuation of U.S. patent application Ser. No. 11/259,537 filed on Oct. 25, 2005 which issued as U.S. Pat. No. 8,162,998 on Apr. 24, 2012, and is a continuation of, and claims priority under 35 U.S.C. §120 to, International Application No. PCT/CH2004/000095, filed Feb. 23, 2004. The entire content of both applications is expressly incorporated herein by reference thereto.

TECHNICAL FIELD

The invention generally relates to a device for fixing bones.

BACKGROUND OF THE INVENTION

It is known in the art to use bone screws for fixing bones. German document DE-A 35 38 238 discusses a bone screw which interacts with a dowel. The dowel is anchored first separately in the bone and then a bone screw is screwed into the dowel. This may connecting two bone fragments in accordance with the dowel/screw principle, which is also known from general fastening techniques.

Also known in the art are transverse locking screws used in conjunction with medullary pin. However, such locking screws have some amount of clearance with respect to the transverse borehole of the medullary pin.

SUMMARY OF THE INVENTION

In the case of the present invention, a fixation of two bone fragments is not the primary objective and is realized only secondarily by means of a medullary pin. Instead, a primary objective of the present invention is to anchor a bone screw stably in a transverse borehole of a medullary pin. The present invention provides a remedy for the above disadvantage/problem. It is an object of the invention to provide a bone screw, which can be brought into the transverse borehole of a medullary pin without any clearance.

The objective is accomplished with a bone screw having a distal end and a proximal end, which has the distinguishing features of a shaft with a core diameter "k" and having an external thread with an external diameter "d". The external diameter "d" of the thread or the core diameter "k" of the shaft tapers in a middle region of the shaft from a larger dimension "$d_2$" or "$k_2$" respectively towards the distal end to a smaller dimension "$d_1$" or "$k_1$", respectively, where "$d_1$" and "$k_1$" do not equal zero. Further, the shaft is provided with a concentrically disposed, radially expandable sleeve, and the sleeve being positioned on the part of the shaft which has the smaller external diameter "$d_1$".

In one embodiment, the thread has a constant depth and the core diameter "k" decreases in the middle region in the direction of the distal end from a larger value "$k_2$" to a smaller value "$k_1$", where and "$k_1$" do not equal zero.'

In another embodiment, the sleeve has an internal thread.

In still a further embodiment, the sleeve has at least one longitudinal slot. The at least one longitudinal slot may extend over the whole length of the sleeve. Alternatively, the at least one longitudinal slot may extend over a portion of the length of the sleeve.

In a further embodiment, the sleeve may have several longitudinal slots. The longitudinal slots may extend over a portion of the length of the sleeve where openings of the longitudinal slots positioned alternatingly at the top and bottom of the sleeve.

In still a further embodiment, the sleeve may have a diameter $D_H$ has a peripheral, encircling flange with an enlarged diameter $D_F$, where $D_F$ is greater than $D_H$ at one of its ends.

In still a further embodiment, the sleeve consists of a non-absorbable plastic, preferably of PEEK. Alternatively, the sleeve may consist of a metallic material. Furthermore, the sleeve may consist of a bio-absorbable plastic.

In a further embodiment, a part of the shaft disposed between the proximal end of the bone screw and the region of the shaft having an external thread diameter of "$d_2$" has a diameter of "$d_3$" such that $d_3 > d_2$, where the part of the shaft having a diameter of "$d_3$" has an external thread.

In another embodiment, a device for bone fixation includes one or more bone screws with a sleeve, and one or more medullary pins. The sleeve may have a continuous diameter $D_H$ and a length $H_L$. The one or more medullary pins may have a longitudinal axis, a diameter $D_N$, a transverse borehole extending transversely to its longitudinal axis, where the transverse borehole has a diameter $D_B$ which is larger than $d_2$ as well as larger than $d_{B-L5}$.

In one embodiment, the diameter $D_H$ of the sleeve fulfills the condition that $D_H \leq 1.2 D_B$.

In another embodiment, the length $H_L$ of the sleeve is more than $1.5 D_N$.

In still a further embodiment, the length $H_L$ of the sleeve is greater than $0.2 D_N$.

The medullary pin may have a continuous cannulation and a wall thickness $W_N$.

In a further embodiment, the length $H_L$ of the sleeve corresponds to the wall thickness $W_N$ of the medullary pin.

BRIEF DESCRIPTION OF THE DRAWING

The present invention can be better understood by reference to the following drawings, wherein like reference numerals represent like elements. The drawings are merely exemplary to illustrate certain features that may be used singularly or in combination with other features and the present invention should not be limited to the embodiments shown.

FIG. 2 shows a longitudinal cross-section of the bone screw of FIG. 1 inserted in a medullary pin with a transverse borehole;

FIG. 5 shows a perspective view of an alternate embodiment of the sleeve of FIG. 1.

DESCRIPTION OF THE PREFERRED EMBODIMENTS

Figure 1:
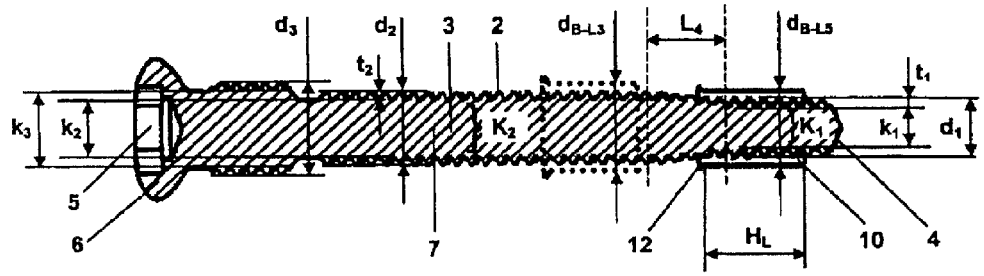
FIG. 1 shows a longitudinal cross-section of a bone screw with a sleeve mounted thereon.
Figure 3:
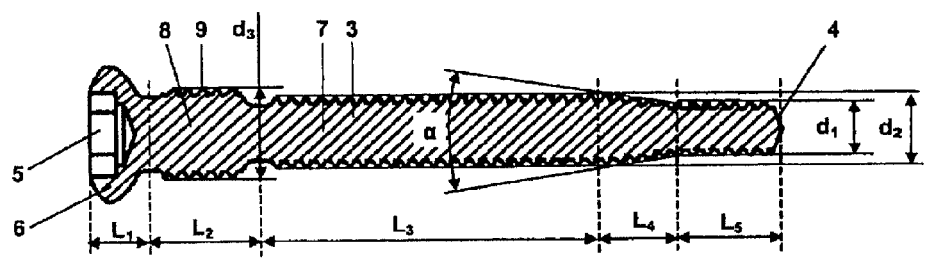
FIG. 3 shows a longitudinal cross-section of the bone screw of FIG. 1.

An embodiment of the bone screw of the present invention is depicted in FIGS. 1 and 3. The bone screw 1, having a core 7 with a diameter "d", includes a shaft 3, a distal end 4 and a proximal end 5 with a screw head 6. The shaft 3 may include external threads 2. The external threads 2 may be configured so that the thread depths $t_1$ and $t_2$ on the segments with lengths $L_5$ and $L_3$ are identical. The bone screw 1 has five segments, which are disposed axially behind one another, these segments being formed as follows.

The screw head 6 extends a length $L_1$, measured from the proximal end 5. Adjoining thereon, a shaft part 8 with a constant external diameter $d_3$ and an external thread 9 having a constant core diameter $k_3$ extends a length $L_2$. Adjoining onto the shaft part 8 is a segment of the shaft 3 with a constant external diameter $d_2$, where $d_2$ is less than $k_3$, and a thread 2 having a constant core diameter $k_2$ extending a length $L_3$. Adjoining thereon, is another segment of the shaft 3, tapering at an angle α towards the distal end 4, and extending a length $L_4$ so that the external diameter $d_2$ of the thread decreases in this segment to an external diameter $d_1$. Likewise, the core diameter $k_2$ decreases in this segment to a core diameter $k_1$. A segment of the shaft 3 with the one constant external diameter $d_1$ and also a thread 2 having a constant core diameter $k_1$ extends between the segment of the length $L_4$ and the distal end 4.

Figure 4:
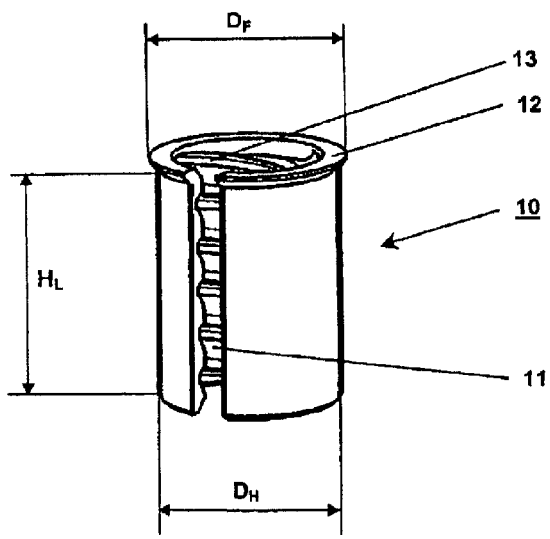
FIG. 4 shows a perspective view of the sleeve of FIG. 1.

A radially expandable sleeve 10 may fit over part of the shaft 3 of the bone screw 1. The sleeve as depicted in FIG. 4 may have a length $H_L$, and a continuous diameter $D_H$. The proximal end of the sleeve 10 may have a flange 12 with a diameter $D_F$.

The outer casing of the sleeve 10 may be formed with a continuous longitudinal slot 11, from which the sleeve 10 gains its elasticity. Furthermore, the cavity of the sleeve 10 may be provided with an internal thread 13. The axial movement, which produces the radial expansion of the sleeve 10 due to the particular geometry of the conical section of the core in the middle part $L_4$ is generated by the pitch of the internal thread. Rotational or screwing movement is required for introducing the screw into the transverse borehole of a medullary pin 20.

As shown in FIG. 1, the sleeve 10 may be screwed from the distal end 4 of the screw so far over the shaft 3, that the sleeve's proximal end, which is provided with the flange 12, extends into the conical segment of length $L_6$. Due to the conicity, the sleeve 10 is expanded somewhat and has a diameter $d_{B-L5}$ which is greater than $D_H$ (FIG. 1). If the sleeve 10 is further screwed onto the shaft 3, the sleeve 10 (shown by a broken line) may be expanded further by the conical segment of length $L_4$, until it reaches a diameter $d_{B-L3}$ on the segment of length $L_3$ with the external diameter $d_3$.

At one end of the sleeve 10, the flange 12 with external diameter $D_F$ being greater than $D_H$ is disposed for axial contact with a suitable supporting surface. The flange 12 functions as a stop or as a positioning means for the sleeve 10 at the medullary pin 20, so that the bone screw 1, with its comically expanding middle part, must be screwed through the sleeve 10, expanding the latter radially, while the sleeve 10 itself is in contact with the middle part.

The sleeve 10 may, for example, consist of a non-absorbable plastic, preferably of PEEK. The advantages of such a sleeve are biocompatibility, ready produceability, simple installation, and the fact that, if the pin is pulled out, the sleeve can be compressed in the event that it remains hanging in the hole of the pin.

The sleeve may, however, also consist of a metallic material. The advantages here are higher strength, biocompatibility, and the fact that the sleeve may consist of the same material as the medullary pin and the bone screw. However, the metallic sleeve is also more ductile, so that it can flow somewhat, if it is inserted at an angle. Finally, the metallic sleeve has the advantage that fragments are not formed.

The sleeve may also consist of an absorbable plastic. A first advantage lies therein that the angularly stable locking decreases with time. A second advantage lies therein that, in the event that such a sleeve is lost, it is not a serious disadvantage that the sleeve is absorbed over time.

The embodiment of the bone screw 1 together with sleeve 10 shown in FIG. 1, may be introduced into a transverse borehole 22 of a medullary pin 20 (FIG. 2). The medullary pin 20 is provided with a continuous cannulation 23, which extends coaxially with the longitudinal axis 21 of the medullary pin 20 and has an external diameter $D_N$ and a wall thickness $W_N$. The transverse borehole 22 may have a diameter $D_B$, which is larger than $d_2$ as well as larger than $d_{B-L5}$. In one embodiment, diameter $D_B$ may be approximately 90% of the diameter $d_{B-L3}$ of the sleeve 10. The sleeve 10 may be inserted completely into the transverse borehole 22 and, with the flange 12, is in contact with the wall of a facet 24 of the transverse borehole 22.

In one embodiment, the length $H_L$ of the sleeve 10 advantageously corresponds to the wall thickness $W_N$ of the medullary pin 20.

In another embodiment, the diameter $D_H$ of the sleeve 10 advantageously satisfies the condition that $D_H \leq 1.2\, D_B$, and the length $H_L$ of the sleeve should be less than $1.5\, D_N$ and more than $0.2\, D_N$.

In another embodiment of the invention, the thread 2 of the bone screw 1 has a constant depth, the diameter of the core of the shaft, in the middle region $L_4$ decreases towards the distal end 4 from the larger value $k_2$ to the smaller value $k_1$, where $k_1$ is larger than zero. The radial expansion accordingly takes place by way of the expansion of the core diameter. This guarantees a certain clamping force in the transverse borehole of the medullary pin 20. In comparison to an expansion of the external diameter of the thread, the expansion of the core diameter results in a larger mass, which is available for locking the screw.

In another embodiment, the sleeve 10 may have one or more longitudinal slots 11 resulting in the advantage that the radial expansion of the sleeve 10 can be achieved with a lesser expenditure of force or with a smaller torque. Pre-installation of the sleeve 10 on the bone screw 1 equalizes shear forces applied to the sleeve 10, thus subjecting the sleeve 10 to a lower internal stress. If a single longitudinal slot 11 is provided, as shown in FIG. 4, the slot 11 may extend over the whole height of the sleeve 10. However, the longitudinal slot 11 may also extend only over a portion of the height of the sleeve 10. In the case of this embodiment, the slot 11 may be open at one side or closed at both sides. For example, as shown in FIG. 5, several partial slots 11' may also be provided over a circumference of the sleeve 10, the partial slots 11' being open alternately at the top and bottom of the sleeve 10.

In the case of a further embodiment, a shaft part is disposed in the region $L_2$ with an enlarged external diameter $d_3 > d_2$ between the proximal end 5 of the bone screw 1 and that part of the bone screw with an enlarged external diameter $d_2$. This arrangement has the advantage that it closes off the hole drilled in the front corticalis of the bone, so that the flange 12 of the sleeve 10 can be brought through the hole in the first corticalis without expending too much force. Moreover, the shaft part may be provided in the region $L_2$ with an external diameter $d_3 > d_2$ with an external thread. The external thread with the external diameter $d_3$ results once again in a screw-like anchorage in the bone.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

It will be appreciated by those skilled in the art that various modifications and alterations of the invention can be made without departing from the scope of the appended claims. Some of these have been discussed above and others will be apparent to those skilled in the art.

The invention claimed is:

1. A method for bone fixation, comprising the steps of:
   placing a radially expandable sleeve over an elongated shaft of a bone screw;
   simultaneously inserting the bone screw and radially expandable sleeve into a transverse opening extending through a bone fixation device positioned in a bone until the radially expandable sleeve is fully housed within the transverse opening; and
   screwing the bone screw further into the bone relative to the radially expandable sleeve to cause expansion of the radially expandable sleeve within the bone fixation device, thereby locking the sleeve to the bone fixation device.

2. The method of claim 1, wherein the bone screw has an elongated shaft with a core diameter "k" and an external thread with an external diameter "d" and comprises:
   a first elongated part extending from a first end to a second end of the bone screw, the first part having a first length and a uniform external diameter "$d_2$" and uniform core diameter "$k_2$";
   a second elongated part extending from a third end to a distal end of the bone screw, the second elongated part having a second length and a uniform external diameter "$d_1$" and uniform core diameter "$k_1$"; and
   a tapered part extending from the second end to the third end of the bone screw, the tapered part tapering from the larger dimensions "$d_2$" and "$k_2$" respectively towards the smaller dimensions "$d_1$" and "$k_1$", respectively, where "$d_1$" and "$k_1$" do not equal zero.

3. The method of claim 2, wherein the radially expandable sleeve is moved to the expanded configuration by the tapered part of the bone screw.

4. The method of claim 2, further comprising a third elongated part extending from a proximal end of the bone screw to the first end, the third part having a third length and a uniform external diameter "$d_3$" such that $d_3 > d_2$, the third elongated part having an external thread.

5. The method of claim 1, wherein the radially expandable sleeve is positioned over the second elongated part during insertion.

6. The method of claim 5, wherein the radially expandable sleeve comprises an increased diameter peripheral flange at a distal end thereof, the flange preventing the sleeve from being pushed out of the transverse opening of the bone fixation device.

7. The method of claim 6, wherein the transverse opening includes a facet at a first end thereof, the facet being formed to receive the flange therein.

8. The method of claim 1, wherein the radially expandable sleeve comprises internal threading configured to mate with external threading of the shaft of the bone screw.

9. The method of claim 1, wherein the radially expandable sleeve comprises a first longitudinal slot extending through an outer wall thereof in alignment with a longitudinal axis of the sleeve.

10. The method of claim 9, wherein the first longitudinal slot extends over one of a portion of and a full length of the radially expandable sleeve.

11. The method of claim 9, wherein the radially expandable sleeve comprises a second longitudinal slot, the first and second longitudinal slots being positioned alternatingly at proximal and distal ends of the radially expandable sleeve.

12. The method of claim 1, wherein the radially expandable sleeve is formed of one of a non-absorbable plastic, a metallic material and a bio-absorbable plastic.

13. The method of claim 1, wherein the bone fixation device is a medullary pin.

* * * * *